United States Patent [19]
Verdini et al.

[11] Patent Number: 5,521,159
[45] Date of Patent: May 28, 1996

[54] PARTIALLY MODIFIED AND RETRO-INVERTED TETRAPEPTIDES ANALOGUES OF C-REACTIVE PROTEIN FRAGMENTS

[75] Inventors: Antonio S. Verdini; Massimo Pinori; Silvana Cappelletti; Laura Gazerro; Flavio Leoni, all of Sesto S. Giovanni, Italy

[73] Assignee: Italfarmaco S.p.A., Milan, Italy

[21] Appl. No.: 307,580

[22] PCT Filed: Apr. 2, 1993

[86] PCT No.: PCT/EP93/00825

§ 371 Date: Sep. 27, 1994

§ 102(e) Date: Sep. 27, 1994

[87] PCT Pub. No.: WO93/21208

PCT Pub. Date: Oct. 28, 1993

[30] Foreign Application Priority Data

Apr. 16, 1992 [IT] Italy ................... MI92A0939

[51] Int. Cl.⁶ ..................... A61K 38/07; C07K 5/02
[52] U.S. Cl. ............................. 514/18; 530/330
[58] Field of Search ...................... 530/330; 514/18

[56] References Cited

U.S. PATENT DOCUMENTS 4,816,560  3/1989  Verdini et al. ............... 530/323

OTHER PUBLICATIONS

*Biotechnology Newswatch*, Aug. 1, 1994, p. 1 and 4.
*The Washington Post*, Jan. 19, 1993, p. D3.
Cross, A. et al. (1993) Choice of bacteria in animal models of sepsis. *Infection and Immunity* 61, 2741–2747. See entire article.

*Primary Examiner*—Christine M. Nucker
*Assistant Examiner*—Benet Prickril
*Attorney, Agent, or Firm*—Oblon, Spivak, McClelland, Maier & Neustadt

[57] ABSTRACT

Retro-inverted tetrapeptides of formula I

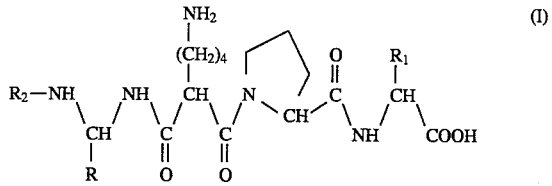

wherein R is a hydrogen atom or the side-chain of threonine; $R_1$ is the side-chain of arginine, leucine or glutamine; and $R_2$ is a hydrogen atom or a metabolically perishable acyl group; with the proviso that when $R_1$ is the side-chain of arginine, R cannot be the side-chain of threonine; diastereo-isomeric forms and pharmacologically acceptable salts, esters and amides thereof. These compounds are useful as immunostimulating agents.

7 Claims, No Drawings

PARTIALLY MODIFIED AND RETRO-INVERTED TETRAPEPTIDES ANALOGUES OF C-REACTIVE PROTEIN FRAGMENTS

The present invention relates to retro-inverted tetrapeptides analogues of C-reactive protein fragments (hereinafter CRP).

CRP is a protein generally having very low blood concentration, which rises up to two thousand times following inflammatory process [J. J. Morley and I. Kushner, Am. N.Y. Acad. Sci., 389, 406–418 (1989)]. F. A. Robey et al , J. Biol. Chem., 262 No.15 7053–7057 (1987) disclose three CRP tetrapeptide sequences very similar to the ones of tuftsin. The chemically sinthetised tetrapeptides show to stimulate the phagocytic leukocytes, to produce superoxide and to induce mononuclear cells to produce interleukin 1, in a qualitatively and quantitatively tuftsin-like manner. Like tuftsin, the three CRP tetrapeptides should be rapidly in vivo metabolised by proteases, and yield peptide metabolites which could competitively inhibit the biological activity/ies of the parent peptides. It has been now surprisingly found that partially modified and N-terminal retro-inverted analogues of said CRP tetrapeptide fragments show not only a considerable stability against the enzymatic degradation while maintaining the immunomodulating activity already seen for tuftsin (see EP-A-0 253 190), but in particular they are able to determine different biological effects depending on the structure and the dose used, specifically in the treatment of septic shock. Therefore the present invention relates to retro-inverted tetrapeptides of the general formula I

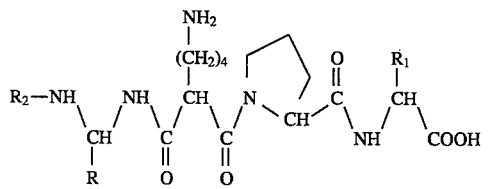

wherein R is a hydrogen atom or the side-chain of threonine; $R_1$ is the side-chain of arginine, leucine or glutamine; and $R_2$ is a hydrogen atom or a metabolically perishable acyl group; with the proviso that when $R_1$ is the side-chain of arginine, R cannot be the side-chain of threonine; and their diastereoisomeric forms and pharmacologically acceptable salts, esters and amides.

Particularly, the invention relates to the retro-inverted tetrapeptides gGly-(R,S)mLys-Pro-Arg, gThr-(R,S)mLys-Pro-Leu, gThr-(R,S)mLys-Pro-Gln, wherein the prefixes g and m mean that the aminoacid is, respectively, a gem-diamine and malonyl residue, and the diastereoisomeric forms thereof.

The retro-inverted tetrapeptides of the present invention are synthesised in accordance with known methods, which the skilled in the art may choose depending on the kind of aminoacids to retroinvert.

For example, when the gem-diamine residue is the 1,1-diaminomethane group (gGly), the retro-inverted tetrapeptide may be prepared by first reacting the Meldrum's acid derivative c-mLys(Z) (i.e. 5-[4-benzyloxycarbonyl]-2,2-dimethyl-1,3-dioxane-4,6-dione) with H-Gly-$NH_2$ in the presence of a sylanising agent such as N,O-bis(trimethylsylyl)acetamide (TSMAc), trimethylsylylchloride (TMS-Cl) or trimethylsylylcianide (TMSCN) (M.J.O. Anteunis & Char. Becu, Bull. Soc. Chim. Belg., 96, 119–139 1986). The second group on the malonyl residue of the pseudopeptide OH-(R,S)mLys(Z)-Gly-$NH_2$(Z=benzyloxycarbonyl) thus obtained is condensed with t-butyl prolinate in the presence of dicyclohexylcarbodiimide (DCC) and 1-hydroxybenzotriazole (HOBT) to give the pseudotripeptide [(R,S)mLys(Z)-Gly-$NH_2$]-Pro-H. Its proline carboxy group is activated with DCC and N-hydroxy-succinimide (HOSu) and reacted with unprotected arginine [Gottlieb, P. et al., Ann. N.Y. Acad. Sci., 419, 12 (1983 )] to obtain the retro-inverted tetrapeptide [(R,S)mLys(Z)-Gly-$NH_2$]-Pro-Arg-OH. The purification is then effected through RP-DC deplacement chromatography, and by this way it is also possible to yield the separation of diastereoisomers, if desired. The purified product is catalytically hydrogenated by HCOOH in the presence of palladium, to remove the remaining protective groups, and then treated with [I,I-bis(trifluoroacetoxy)-iodo]benzene (TIB) for turning the glycine carboxamide into the N-terminal residue of gGly. One last purification by ion exchange chromatography enable to obtain the final product as acetate.

Another example is where threonine is the gem-diamine residue. The synthesis of the retro-inverted tetrapeptide starts from a C-terminal dipeptide obtained through condensation of Z-Pro-OH and H-Y-OtBu, wherein Y represents the aminoacid Leu or Gln in accordance with what said in the definition of formula I, optionally suitably protected, and through subsequent removal of the benzyloxycarbonyl group by catalytic hydrogenation. Such dipeptide is reacted with the N-terminal retro-inverted dipeptide prepared, as described, for example, in the Italian patent application No. 21349 A/90.

MNP-Thr(tBu)-OH obtained by acylating previously sylanised H-Thr(tBu)-OH with MNP-COOH, in the presence of suitable carboxy-activating agents, is treated with biphenylphosphorazide (DPPA) yielding the relevant azide, which gives the isocianate by heating. This is treated with tiophenol in the presence of catalytic amounts of amine, preferably a tertiary amine such as triethylamine or diisopropylamine, to obtain the phenylthiocarbonyl derivative MNP-gThr(tBu)-PTC. Subsequently the amine residue is deprotected, for example, by treatment with diluted sodium hydroxide to give MNP-gThr(tBu)-H. The condensation of this latter with c-mLys(Boc) gives the N-terminal pseudo-dipeptide MNP-gThr(tBu)-(R,S)mLys(Boc) which, in its turn, is condensed with H-Pro-Y-OtBu, wherein Y is as defined above, in the presence of DCC/HOBT to give the protected retro-inverted tetrapeptide of formula I wherein R is 1-hydroxyethyl. By means of treatment with an acid, all the protective groups are removed except for the one of the gem-diamine residue. At the same time as the purification via RP-DC, it is possible to separate the two diastereoisomers, if desired. The MNP group may be removed through catalytic hydrogenation, for example, by using ammonium formate on sponge Pd. The retro-inverted tetrapeptide is submitted to the final purification by suitable chromatographic methods.

Preparative examples of some retro-inverted tetrapeptides representative of the claimed class are herein provided, which are not to be intended as limiting the invention in any way.

The HPLC analysis of the aminoacid derivatives, of the protected fragments and of the retro-inverted tetrapeptide is carried out under the following experimental conditions:

column: Lichrosorb RP-18;

flow: 1.5 ml/min;

detector: Merck L-4200 UV-VIS (230 or 254 nm);

eluent A: water 90%, MeCN 10%, trifluoroacetic acid (TFA) 0.1%;

eluent B: MeCN, TFA 0.1%;

eluent C: water, TFA 0.1%;
Graidents:
- (I): from 0 to 40% B in A (20'), to 80% B in A (10')
- (II): from 37 to 80% B in A (20')
- (III): from 0 to 50% A in C (20'), to 100% A (3'), to 40% B in A (20')
- (IV): from 10 to 40% A in C (8'), to 100% A (2'), to 40% B in A (20')

In the ion exchange purifications, the FPLC system of Pharmacia equipped with LKB UVICORD S II detector with filter at 226 nm, Pharmacia recorder (chart speed=0.1 cm/min) and Pharmacia FRAC 200 fraction collector is employed.

The aminoacid and $NH_3$ compositions and ratios (as specific datum of the gem-diamino residue) of the various retro-inverted peptides are determined by Beckman SYSTEM GOLD automatic aminoacid analyzer after hydrolysis with HCl 6M at 110° C. for 22 hours.

The alphanumeric code in bracket after the name of some compounds is an internal code of indentification.

EXAMPLE 1

H-gGly-(R,S)mLys-Pro-Arg-OH.2AcOH (ITF 1127)

A) A suspension of H-Gly-$NH_2$.HCl (3.32 g, 30 mmoles) in THF (200 ml) was added with TMSAc (19.6 ml, 80 mmoles) and TMS-Cl (2.54 ml, 20 mmoles) in sequence. After 30 minutes c-mLys(Z) (6.98 g, 20 mmoles) was added, and the reaction mixture was stirred at room temperature for further 3 hours. The solvent was evaporated under vacuum and the residue was taken up with water (200 ml) while adjusting the pH to 3 with HCl 0.1N. After 1 hour under stirring at room temperature, the formed solid was filtered, washed with water, and dissolved in hot ethanol. The solid obtained after cooling was filtered, washed with ethyl ether and dried. 3.8 g of (R,S)mLys(Z)-Gly-$NH_2$ were obtained (yield: 51%).

HPLC [gradient (I) (254 nm)]: r.t. 13.5 minutes; purity 98%; m.p.: 161° C. (dec.)

The $^1$H-NMR confirmed the structure of the product.

B) A solution of the product under A) (3.65 g, 10 mmoles) in DMF (15 ml), cooled in iced bath, was added with HOBT (1.43 g, 10.5 mmoles) and DCC (1.96 g, 9.5 mmoles) in sequence. After 30 minutes under stirring, the mixture was filtered and the filtrate was added to a solution of DMF (10 ml) containing HCl.H-Pro-OtBu (2.49 g, 12 mmoles) and TEA (1.67 ml, 12 mmoles). The mixture was stirred for 3 hours, then the solvent was evaporated under vacuum, the residue was taken up with ethyl acetate (50 ml), and the organic phase was washed with potassium bisulphate 2%, sodium hydrocarbonate 5%, and neutralised with water, then anhydrified on sodium sulphate. The obtained 4.2 g of a light oil (yield: 82%) were dissolved in a mixture of DMC and TFA (1:1 v/v, 16 ml) and stirred for 1 hour. The solvent was evaporated under vacuum, and the residue was ground with ethyl acetate and ethyl ether to obtain 3.6 g of [(R,S)mLys(Z)-Gly-$NH_2$]-Pro-OH as white solid (yield: 79%).

HPLC [gradient (I) (254 nm)]: r.t. 14.6 and 15.7 minutes (two diastereoisomers); purity 97%.

The $^1$H-NMR confirmed the structure of the product.

C) A solution of the product under B) (3.36 g, 7.5 mmoles) in THF (50 ml), was added with HOSu (0.95 g, 8.25 mmoles) and, after cooling to −10° C., with DCC (1.54 g, 7.5 mmoles). After 4 hours under stirring at room temperature, the reaction mixture was filtered and the filtrate added to a solution of DMF/water (7:3 v/v, 125 ml) containing H-Arg-OH (1.74 g, 10 mmoles) and KCl (0.74 g, 10 mmoles). The reaction mixture was kept under stirring for 90 minutes at room temperature, then the solvent was evaporated under vacuum, and the residue was washed some times with ethyl ether and dried. The solid obtained was dissolved in an aqueous solution of TFA (0.16 v/v, 30 ml) and purified through RP-DC in three aliquots. In each purification 10 ml of solution were charged on a Dynamax 300 Å $C_{18}$ (21.4×300 mm) column previously balanced with water containing TFA (0.1% v/v), at a flow of 2.7 ml/minute. At the end of the charging the column was eluted, still at 2.7 ml/minute, with an aqueous solution 50 mM of benzyldimethylhexadecylammonium chloride (BDHA-Cl) containing TFA (0.1% v/v). After about 1 hour of elution, 2.7 ml fractions were collected. The fractions were analyzed by HPLC [gradient (I)], and the ones containing impurities were eliminated, while the others were collected in three groups respectively containing isomer A, the mixture of the two isomers, and isomer B of the compound [mLys(Z)-Gly-$NH_2$]-Pro-Arg-OH. At the end of the three chromatographies, the three groups of fractions were freeze-dried yielding 1.9 g of isomer A, 0.45 g of the isomeric mixture and 1.8 g of isomer B (total yield: 89%).

HPLC [gradient (I) (220 nm)]: r.t. 13.6 minutes (isomer A), purity: 96%; r.t. 14.7 minutes (isomer B); purity 93%+ 4% of isomer A.

FAB-MS: m/z=619 amu [M+H]$^+$; m/z=485 amu [M−Z+ H]$^+$ (identical spectra for the two isomers).

D) Fresh sponge Pd (about 0.1 g) was added to a solution of the isomer mixture under C) (0.31 g, 0.5 mmoles) in formic acid (85%, 5 ml), and the mixture was slowly stirred at room temperature for 90 minutes. After filtering off the catalyzer, the solvent was evaporated under vacuum and the residue taken up with water and freeze-dried. The solid obtained was dissolved in a mixture of DMF/water (3:1 v/v, 5 ml) and added with TIB (0.43 g, 1 mmole). The reaction mixture, sheltered from the light, was stirred at room temperature for 16 hours. The solvent was evaporated under vacuum and the residue dissolved in water, washed with ethyl ether and freeze-dried. The solid obtained was dissolved in water at pH 6 and charged (flow=1 ml/minute) on a column (6×200 mm) filled with CM-52 carboxymethylcellulose and previously balanced with a solution of ammonium acetate 15 mM at pH 6. After charging, the column was eluted with a linear gradient of ammonium acetate from 0.15 mM to 150 mM within 6 hours, at a flow of 1 ml/minute, while maintaining pH at 6. Fractions of 3 ml were collected and analyzed by HPLC [gradient (III)]: the fractions contaning the product in title (ITF 1127) were collected and freeze-dried more times. The solid obtained was dissolved in absolute ethanol and 0.085 g of product precipitated by adding ethyl ether to obtain (yield: 30%).

HPLC: [gradient (III)]: r.t. 8.8 (isomer A) and 10.2 (isomer B) minutes; purity 99%.

FAB-MS: m/z=457 amu [M+H]$^+$

Following an analogous procedure 0.425 g was obtained (yield: 30%) of isomer A (ITF 1357)

$^1$H-NMR (200 MHz; DMSO)

t (1H; NHG) 8.25; d (1H; NH-R) 7.20; m (1H; $C_\alpha$P) 4.30; m (4H; αG; αR; $\delta_A$P) 3.93÷3.64; m (3H; $\delta_B$P; δK)

3.61÷3.37; t (2H; δR) 3.04; t (2H; εK) 2.74; m (6H; βP; τP; βK) 2.09÷1.79; s (6H CH₃COOH) 1.75; m (8H; δK; τK; βR; τR) 1.70÷1.18.

Following the procedure for isomer A it was obtained 0.45 g of product as isomer B (ITF 1358) (yield: 32%) and 0.1 g of mixture (ITF 1127).

HPLC: [gradient (III)]: 10.2 minutes; purity 96%+ isomero A.

FAB-MS: m/z=457 amu [M+H]

¹H-NMR (200 MHz; DMSO)

t (1H; NGH) 8.30; d (0.4H; NHR) 7.57; d (0.6H; NHR) 7.47; m (1H; C$_\alpha$H) 4.43; m (3H; αG; αR) 3.97÷3.82; m (4H; δP; δK) 3.63÷3.33; m (2H; δR) 3.06; m (2H; εK) 2.72; s (6H CH₃COO⁻) 1.76; m (14H; β,τP; β,τ,δK; β,τR) 1.21÷1.15.

EXAMPLE 2

H-gThr-R,S)mLys-Pro-LeU-OH.AcOH (ITF 1192)

A) A solution of bis(trichloromethyl)carbonate (3.71 g, 12.5 mmoles) in methylene chloride (125 ml) at 0° C. was added with 1-methylimidazole (5.96 ml, 75 mmoles) in 80 ml of methylene chloride. After 5 minutes MNP-OH (5.63 g, 25 mmoles) dissolved in methylene chloride (80 ml) was added and, after further 5 minutes, it was followed by H-Thr(tBu)-OH (5.26 g, 30 mmoles) previously sylanized with TMSCN (11.3 ml, 90 mmoles), and further 200 ml of methylene chloride. After 10 minutes, the reaction mixture was washed with an aqueous buffer acidified to pH 3.5, anhydrified and evaporated to dryness. The residue taken up with sodium carbonate 5% (300 ml) was washed with methylene chloride. The aqueous phase was added with further 200 ml of ethyl acetate and the pH brought to 5.7. The organic phase was separated and anhydrified, and the solvent evaporated to obtain MNP-Thr(tBu)-OH as an oil (6.5 g, yield: 68%).

HPLC [gradient (I) (254 nm)]: r.t. 25.1 minutes; purity: 88%.

B) A solution of the compound under A) (5.2 g, 13.6 mmoles) in anhydrous toluene (50 ml) at 0° C. was added with DPPA (3.22 ml, 14.9 mmoles) and TEA (2.09 ml, 14.9 mmoles). After 4 hours the reaction mixture was washed three times with a solution saturated with sodium hydrocarbonate and with a solution saturated with sodium chloride, both the solutions being pre-cooled to 0° C., then it was anhydrified. The solution containing the azide was heated to 80° C. and maintained at such temperature for 40 minutes. The formed isocianate was added with tiophenole (1.39 ml, 13.6 mmoles) and a catalytic amount of TEA (191 ul, 1.36 mmoles), at room temperature. After one night, the mixture was treated with ethyl acetate and water, and the organic phase was washed with potassium bisulphate 2%, sodium hydrocarbonate 5% and neutralised with water, then anhydrified on sodium sulphate, evaporated to dryness and the oil obtained was ground with petroleum ether. There were obtained 4.7 g of MNP-gThr(tBu)-PCT (yield: 71.2%). HPLC [gradient (II) (254 nm)]: r.t. 14.9 minutes; purity: 95%.

C) A mixture of sodium hydroxide (1M, 26 ml) and water 877 ml) maintaned at 0° C. was slowly added with a solution of the compound under B) (4.7 g, 9.6 mmoles) in THF (64 ml). After 5 minutes from the end of the addition, the reaction mixture was neutralised with HCl (1M, 26 ml). The THF was evaporated, and chloroform (80 ml) was added and the pH of the biphasic mixture was brought to 9.0 with sodium hydroxide 1M. The organic phase was separated off and the aqueous one was treated with chloroform three times, while adjusting the pH to 9.0 each time: the organic phases were collected and evaporated to dryness. The residue resuspended in ethyl ether was added with water (50 ml) and the mixture was titrated to pH 3.5 with HCl 1M until constant pH. The aqueous phase was separated and the treatment repeated twice. The collected aqueous phases were freeze-dried to obtain 2.8 g of MNP-gThr(tBu)-H.HCl (yield: 85%).

HPLC [gradient (I) (254 nm)]: r.t. 16.43 minutes; purity: 99.9%.

D) A solution of the compound under C) (2.6 g, 6.6 mmoles) and c-mLys(Boc) (2.4 g, 8 mmoles) in THF (120 ml) was slowly added with TMSAc (4.6 ml, 20 mmoles). After 20 hours the reaction mixture was evaporated and the residue taken up with water and brought to pH 3.5 with HCl 1M in the presence of ethyl acetate. The aqueous phase was estracted three times with ethyl acetate, and the collected organic phases were anhydrified, reduced to a small volume, and added with diisopropyl ether to give 3.4 g of MNP-gThr(tBu)-(R,S)mLys(Boc)-OH (yield: 85%).

HPLC [gradient (II) (230 nm)]: r.t. 9.9 and 10.2 minutes (two diastereoisomers); purity 93%.

E) A solution of Z-Pro-OH (2.4 g, 10 mmoles) and H-Leu-OtBu.HCl (2.7 g, 12 mmoles) in methylene chloride (50 ml) was added with TEA (3 ml, 22 mmoles) followed by BOP (4.4 g, 10 mmoles) and HOBT (1.35 g, 10 mmoles). After 5 hours the reaction mixture was treated once with a solution saturated of sodium chloride, then evaporated to dryness. The residue was divided between ethyl acetate and water. The organic phase was washed with potassium bisulphate 2%, sodium hydrocarbonate 5%, neutralised with water and anhydrified on sodium sulphate, then dried, and from the residue dissolved in diisopropyl ether 3.8 g of Z-Pro-Leu-OtBu were obtained by addition of petroleum ether (yield: 92.7%).

HPLC [gradient (I) (230 nm)]: r.t. 28.6 minutes; purity 100%.

F) The dipeptide under E) (1.5 g, 3.5 mmoles) was dissolved in methanol (70 ml) and this solution, under nitrogen, was added with Pd/C catalyzer (100 mg) and then, very slowly, with triethylsylane (2.9 ml, 18 mmoles). After 3 hours the reaction mixture was filtered and the solvent evaporated, thus obtaining 1 g of H-Pro-Leu-OtBu (yield: 100%).

HPLC [gradient (I) (230 nm)]: r.t. 15.9 minutes; purity 93%.

G) A solution of the pseudodipeptide under D) (1.1 g, 1.9 mmoles) in methylene chloride (15 ml) was added with HOBT (320 mg, 2.3 mmoles) dissolved in 200 ml of DMF. The temperature was brought to 0° C. and DCCI (392 mg, 1.9 mmoles) was added. After 15 minutes the mixture was filtered in a flask containing the C-terminal dipeptide under E) (540 mg, 1.9 mmoles) and left to react overnight. After evaporating the solvent, the residue was divided between ethyl acetate and water, and the organic phase was washed with potassium bisulphate 2%, sodium hydrocarbonate 5% and neutralised with water, then anhydrified on sodium sulphate. From the dried organic phase by grinding of the residue with diisopropyl ether 12.3 g of MNP-gThr(tBu)-(R,S)mLys(Boc)-Pro-Leu-OtB were obtained (yield: 77%).

HPLC: isocratic from 65% of B (230 and 254 nm): r.t. 8.2 and 8.6 minutes; purity: 100%.

H) An aliquot of the compound under G) (1.4 g, 1.3 mmoles) was treated in iced bath with concentrated HCl (5 ml) for 8 minutes. The reaction mixture was evaporated to dryness, then taken up with water and freeze-dried. There were obtained 910 mg of a crude that was purified through RP-DC on a Dynamax colummn (300 Å C18, 12 um, 21×250 mm) employing benzyl-dimethyldodecylammonium bromide (BDDA-Br, 50 mM in 90% of water, 10% of acetonitrile and 0.1% of TFA) as displacer, at a flow of 2.7 ml/minute. Thus three fractions of MNP-gThr-mLys-Pro-Leu-OH were recovered: 320 mg of isomer A, 320 mg of isomer B and 160 mg of diastereoisomeric mixture.

HPLC [gradient (I) (230 nm)]: r.t. 16.1 and 18 minutes; purity 99.9%.

I) The isomer A under H) (315 mg, 0.4 mmoles) was dissolved in methanol (15 ml) and added with sponge Pd activated with formic acid and a solution of ammonium formate (120 mg) in formic acid (5 ml). After 2 hours the catalyzer was filtered off and, after evaporation of the solvent, the residue was taken up with water. The aqueous phase was washed with ethyl ether and freeze-dried yielding 200 mg of a crude that was purified by ion exchange on a Pharmacia XK16 column (16×200 mm) of S-Sepharose Fast Flow employing ammonium acetate 0.015M, pH 6.0 (A) and ammonium acetate 0.3M, pH 6.0 (B) as eluent in linear gradient from 0 to 25 % of B in A (30') and then in isocratic for 40 minutes, at a flow of 3 ml/minute. The fractions collected every 2 minutes were analized by HPLC and the ones containing the product in title were freeze-dried.

HPLC [gradient (III) (230 nm)]: r.t. 12.8 minutes; purity 97%.

Aminoacidic composition: Pro(1) 1.0; Leu(1) 1.0; $NH_3$ (2) 1.9; peptide content: 77 umoles (40 mg; yield: 20%).

$^1$H-NMR (200 MHz; $^1$H-DMSO; 30° C.) (isomer A -ITF 1432): d (1H; NH-$_g$T) 7.79; d (1H; NH-L) 6.93; In (2H; Cα-P, Cα-$_g$T) 4.31÷4.21; q (1H; Cα-L) 3.84; m (1H; Cδ-P) 3.74; In (3H; Cδ$^2$P; Cβ-$_g$T; Cα-mK) 3.63÷3.37; In (2H; Cε-mK) 2.75; m (4H; Cβ,Cτ-P) 2,19÷1,74; m (9H; Cβ,Cτ, Cδ-mK; Cβ,Cτ-L) 1.73÷1.13; d (3H; Cτ-$_g$T) 1.06; d (3H; Cδ$^1$L) 0.88; d (3H; Cδ$^2$L) 0.87.

Following the same procedure applied for isomer, isomer B (ITF 1443) was obtained:

$^1$H-NMR (200 MHz; $^1$H-DMSO; 30° C.) d (0.9.; N$^A$H-$_g$T) 8.13; d (0.1H; N$^B$H-$_g$T) 8.03; d (0.1H; N$^B$H-L) 7.45; d (0.9H; N$^A$H-L) 7.36; m (2H; Cα-P, Cα-$_g$T) 4.37÷4.24; m (1H; Cα-L) 3.86; m (3H; Cδ-P; Cβ-$_g$T) 3.56÷3.38; m (1H; Cβ-mK) 3.16; m (2H; Cε-mK) 2.76; m (13H; Cβ,Cτ-P; Cβ,Cτ,Cδ-mK; Cβ,Cτ-L) 2.23÷1.15; d (3H; Cτ-$_g$T) 1.03; d (6H; Cδ-L) 0.88.

EXAMPLE 3

H-gThr-(R,S)mLys-Pro-Gln-OH.AcOH (ITF 1193)

A) Z-Gln-OH (5.6 g, 20 moles) was dissolved in glacial acetic acid (60 ml) and added with Trt-OH (Trt=trityl) (10.4 g, 40 mmoles), Ac$_2$O (3.77 ml, 40 mmoles) and sulphuric acid. The reaction mixture was heated to 50° C. and kept at this temperature for 90 minutes, then cooled to room temperature and treated with water. The precipitate obtained was filtered, suspended in water and extracted three times with ethyl acetate. From the collected and anhydrified organic phases 8.12 g of Z-Gln(Trt)-OH precipitated by concentration and addition of n-hexane (yield: 77%).

HPLC [gradient (II) (230 nm)]: r.t. 11.3 minutes; purity: 100%.

B) A solution of the product obtained under A) (4 g, 7.6 mmoles) in methylene chloride (50 ml) was added with borotrifluoro etherate (153 ul) and t-butyl-2,2,2-trichloroacetimidate (TBTA; 4.2 g, 15.3 mmoles). After 10 minutes the reaction mixture was washed once with a solution saturated with sodium hydrocarbonate and water, then anhydrified and evaporated to dryness. The residue obtained was dissolved in methanol (60 ml) and 3.5 g of Z-Gln(Trt)-OtBu precipitated by addition of water (yield: 81%).

HPLC [gradient (II) (230 nm)]: r.t. 17.7 minutes; purity: 100%.

C) A solution of the compound under B) (2.5 g, 4.3 mmoles) in 200 ml of methanol, saturated with nitrogen, was added with sponge Pd activated with formic acid, and a solution of ammonium formate (200 mg in 5 ml). After 3 hours the catalyzer was filtered off and the methanol solution evaporated to dryness. The residue was taken up with ethyl acetate, washed once with sodium hydrocarbonate 5% and then neutralised with water. The organic solution was anhydrified and concentrated to small volume, then cooled to 0° C. and treated with 1 equivalent of HCl in ethyl acetate (4M, 1.08 ml). By subsequent addition of petroleum ether 2 g of HCl.H-Gln(Trt)-OtBu precipitated (yield: 100%).

HPLC [gradient (II) (230 nm)]: r.t. 7.4 minutes; purity: 100%.

D) Z-Pro-OH (1.15 g, 4.6 mmoles) was dissolved in methylene chloride (15 ml) and added with HOBT (0.7 g, 5.5 mmoles) in DMF (250 ul). This solution, in iced bath, was added with DCCI (0. 95 g, 4.6 mmoles). After 15 minutes the reaction mixture was filtered in a flask containing the compound under C) (2 g, 4.1 mmoles) and neutralised with TEA (58 ul, 4.1 mmoles) . After 18 hours, the solvent evaporated, and the residue was divided between ethyl acetate and water, the organic phase was washed with potassium bisulphate 2%, sodium hydro carbonate 5% and neutralised with water, then anhydrified on sodium sulphate. From the organic solution concentrated to small volume 2.6 g of Z-Pro-Gln(Trt)-OtBu were obtained by addition of n-hexane (yield: 93%).

HPLC [gradient (II) (230 nm)]: r.t. 16.8 minutes; purity: 100%.

E) The protected dipeptide under D) (2.4 g, 3.5 mmoles) was hydrogenated in 100 ml of methanol by sponge Pd and formic acid, as under C). After filtering off the catalyzer and evaporating methanol, the residue was taken up with ehtyl acetate, washed once with sodium hydrocarbonate 5% and anhydrified. The concentrated organic phase was treated with HCl in ethyl acetate (4M, 875 ul) at 0° C., and 2 g of HCl.H-Pro-Gln(Trt)-OtBu were obtained by adding petroleum ether (yield: 100%).

HPLC [gradient (II) (230 nm)]: r.t. 7.8 minutes; purity: 100%.

F) A solution of the pseudodipeptide obtained under Example 2,D) (1.38 g, 2.26 mmoles) in methylene chloride (15 ml) was added with HOBT (382 mg, 2.82 mmoles) dissolved in 200 ul of DMF. The temperature was brought to 0° C. and DCCI (466 mg, 2.26 mmoles)

was added. After 15 minutes the mixture was directly filtered in a flask containing the dipeptide under E) (1.31 g, 2.26 mmoles), neutralised with TEA (318 ul, 2.26 mmoles) and left to react overnight. After evaporation of the solvent, the residue was divided between ethyl acetate and water, the organic phase was washed with potassium bisulphate 2%, sodium hydrocarbonate 5%, and neutralised with water, then anhydrified on sodium sulphate. The organic phase was evaporated to dryness and then taken up with ethyl acetate/n-hexane (1:1 v/v, 15 ml), and 2.3 g of MPN-gThr(tBu)-(R, S)mLys(Boc)-Pro-Gln(Trt)-OtBu were obtained by addition of n-hexane (yield: 92%).

HPLC [gradient (II) (230 nm)]: r.t. 21.5 and 22.0 minutes (two diastereoisomers); purity: 92.5%.

G) The retro-inverted tetrapeptide under F) (2.13 g, 1.87 mmoles) was dissolved in methylene chloride/TFA (1:1 v/v, 40 ml) at room temperature. After 90 minutes, the solvent was evaporated, the crude precipitated by addition of ethyl ether. Thus 1.416 g of MPN-gThr-(R, S)mLys-Pro-Gln-OH were obtained (yield: 95%).

HPLC [gradient (I) (230 nm)]: r.t. 12.4 minutes; purity: 91.5%.

Aminoacidic composition: Pro(1) 1.0; Gln(1) 1.0; $NH_3$(3) 2.9; peptide content: 92.7%. The protected retro-inverted tetrapeptide was purified by RP-DC un a Dynamax (300 Å C18, 12 um, 21.4×300 mM) column by using BDDA-Br (50 mM in water, 0.1% TFA) as displacer, at a flow of 2.7 ml/minute. Thus 1.04 g of the product were recovered (yield: 81%).

HPLC [gradient (I) (230 nm)]: r.t. 12.4 minutes; purity: 100%. In a gradient from 0 to 20% in A (20 minutes): r.t. 17.5 and 17.8 minutes (two diastereoisomers); purity: 100%.

H) The protected retro-inverted tetrapeptide under G) (875 mg, 1.1 mmoles) was dissolved in 15 ml of an aqueous solution of ammonium formate (0.25M, pH 3.0), added to sponge Pd activated with ammonium formate (0.5M, pH 3.0), and left to react at 60° C. for 15 minutes. The treatment was repeated four times, raising the reaction temperature to 70° C., until the HPLC showed the disappearance of the starting compound. The catalyzer was then filtered off, and the aqueous phase was washed with ethyl ether and freeze-dried. The crude was purified through ion exchange on a Pharmacia XK26 column (26×300 mm) of CM-Sephadex C-25 by employing ammonium acetate 0.015M, pH 6.0 (A) and ammonium acetate 0.3M, pH 6.0 (B) as eluent with a linear gradient from 0 to 100% of B (360 minutes, at a flow of 4 ml/minute. Fractions of 3.7 ml were collected: there were freeze-dried the ones that had shown to contain the product in title. HPLC [gradient (IV) (230 nm)]: r.t. 6.5 and 7.7 minutes (two diastereoisomers in a ratio 1:1); purity: 99%.

Aminoacidic composition: Pro(1) 1.0; Gln(1). 1.0; $NH_3$ (3) 2.9; peptide content: 966 umoles (513 mg); yield 88%.
$^1$H-NMR (200 MHz; DMSO)

d (0.5H; NHT) 8.26; d (0.5H; NHT) 7.99; d (0.5H; NHQ) 7.49; s (1H; N Q) 7.31; d (0.5H; NαQ) 7.04; s (1H; NαQ) 6.67; m (1H; $C_\alpha$T) 4.31; m (1H; $C_\alpha$P) 4.22; m (2H; CαQ; CδP) 3.83÷3.70; m (3H; CβT; CαK; Cδ'P) 3.64÷3.34; m (2H; CτK) 2.74; m (8H; CβP; CβK; Cβ e CτQ) 2.17÷1.66; s (6H $CH_3COOH$) 1.85; m (6H; CτP; Cτ e CδK) 1.64÷1.12; t (3H; CτT) 1.04.

Some compounds representative of the invention were tested for the biological activity thereof.

Stimulation of in vitro IFN-τ production by murine splenocytes

The splenic cells were obtained from spleen of BALB/C mice as single cells suspension. The splenocytes thus obtained were resuspended in RPMI 1640 culture medium (Flow Lab., Hertz, UK) containing 5% of fetal calf serum (FCS) (HyClone, ST, Utah, USA) at a final concentrazione of $10^7$ cells/ml, and incubated in 96-well plates for 24 hours at 37° C. in the presence of the tested compounds at the indicated concentration. At the end of the incubation the supernatant was collected, filtered by 22 μm filter and freezed to −80° C. until the time of the test carried out by ELISA commercial kit (Genzyme, Boston, Mass., USA).

The results are set forth in Table 1.

TABLE 1

| | U/ml (Stimulation index) | | |
|---|---|---|---|
| Dose (μg/ml) | Ex.1 | Ex.2 | Ex.3 |
| 0 (control) | 31 | 31 | 41 |
| 0.1 | 33 (1.1) | 57 (1.8) | 60 (1.5) |
| 1.0 | 60 (1.9) | 52 (1.7) | 60 (1.5) |
| 10.0 | 49 (1.6) | 60 (1.9) | 68 (1.7) |

The results obtained as U/ml and stimulation index (IS) with respect to the control (Untreated cells), showed that the compounds of the invention are able to dose-dependently stimulate IFN-τ production by murine splenocytes. Particularly, the compound of example 1 showed to be the most powerful one of the present class: indeed it doubled the cytokine in question already at a dose of 1.0 μg/ml.

Stimulation of IL-1 production by murine peritoneal macrophages

Murine peritoneal macrophages were obtained by inoculation of a solution of hydrolized starch (BDH Chemicals, Poole, Dorset, UK) into the peritoneal cavity of BALB/C. mice, three days before sacrificing the animals. The peritoneal cells were then collected by washing the peritoneal cavity with a solution of RPMI 1640 containing 10% of FCS, and resuspended in the same solution at a concetration of $10^6$ cells/ml in 96-well plates. The incubation was performed for 96 hours at 37° C. in the presence of the compounds in question. At the end of the treatment the supernatants were collected and used for dosing cytokine by means of a suitable ELISA commerical kit (Genzyme, Boston, Mass., USA).

The results are set forth in Table 2.

TABLE 2

| | U/ml (Stimulation index) | | |
|---|---|---|---|
| Dose (μg/ml) | Ex.1 | Ex.2 | Ex.3 |
| 0 (control) | 15 | 15 | 15 |
| 0.01 | 6 (0.4) | 90 (6.0) | 150 (10.0) |
| 0.1 | 2 (0.1) | 60 (4.0) | 160 (10.7) |
| 1.0 | 2 (0.1) | 47 (3.1) | 155 (10.3) |
| 10.0 | 2 (0.1) | 50 (3.3) | 140 (9.3) |

The results obtained as U/ml and IS with respect to the control, reveal that the tested compounds show a remarkable stimulatory effect. Particularly, the compound of Example 3 increased about ten times (9.3<IS<10.7) the IL-1 production at all the doses used.

Stimulation of the nitric oxide by murine peritoneal cells

The peritoneal cells were obtained as described in the previous test, and incubated for 96 hours at 37° C. in the presence of the compounds in question and of lipopolysaccharide at a concentration of 30 μg/ml. At the end of the treatment the supernatants were collected and the nitric oxide content was determined by the chemiluminescence test described by Palmer R. M. J. et al, Nature, 327, 524, 1987.

The results are set forth in Table 3.

TABLE 3

| Dose (μg/ml) | nmol/ml (Stimulation index) | | |
|---|---|---|---|
| | Ex.1 | Ex.2 | Ex.3 |
| 0 (control) | 20 | 20 | 20 |
| 0.01 | 43 (2.2) | 85 (4.3) | 50 (2.5) |
| 0.1 | 59 (3.0) | 61 (3.1) | 60 (3.0) |
| 1.0 | 77 (3.9) | 66 (3.3) | 66 (3.3) |
| 10.0 | 57 (2.9) | 79 (4.0) | 88 (4.4) |

The results obtained as nmol/ml and stimulation index with respect to the control, show that the compounds of the invention stimulate the nitric oxide production at all the doses used. Particularly, the compound of example 2 showed a stimulation peak already at 0.01 μg/ml (IS=4.3).

Effect on the leishmanicidal activity of murine peritoneal macrophage

The peritoneal cells collected as described above were seeded in 96-well flat bottom plates (Nunc, Roskiled, DK) at a concentration of $10^5/100$ μl; and incubated per 24 hours at 37° C. At the end of the treatment, the cells not adherent to the well were separated and discharged, whereas the adherent cells were washed three time with culture medium and incubated for 24 hours with the compounds in question, then the cells were infected through a 24 hours incubation with promastigotes of Leishmania major (L. major, PVL49 strain supplied by Dr. Neal R. A., London School of Hygiene and Tropical Medicine, London, UK). At the end of the infection treatment each well was added with 100 μl of a 0.01% solution od sodium dodecylsulphate in RPMI 1640, and the plates were incubated for 30 minutes at 37° C. The Schneider's culture medium (Schneider Drosophila medium, Gibco Lab., Grand island, N.Y., USA) with 30% of FCS was added. Each well was added with 1 μCi of $^3$H-thymidine, and a 72 hours incubation was carried out at 37° C. The incorporation of radioactivity by the living parasites inside the peritoneal cells, which is correlated to the infection degree and consequently to the leishmanicidal activity of the cells, was measured by collecting the cells by means of a cell-harvester and measuring the radioactivity with liquid scintillation β-counter.

The results are set forth in Table 4.

TABLE 4

| Dose (μg/ml) | cpm* (% reduciton of infection)** | | |
|---|---|---|---|
| | Es. 1 | Es. 2 | Es. 3 |
| (control) | 18,273 | 18,273 | 18,273 |
| 0.1 | 5,096 (72) | 17,568 (4) | 18,826 (−3) |
| 1.0 | 3,783 (79) | 11,991 (34) | 8,377 (54) |
| 10.0 | 4,292 (77) | 10,582 (42) | 7,842 (57) |

*counts per minute $$xx = 100 - \left[ \frac{\text{cpm treated cells}}{\text{cpm control cells}} \times 100 \right]$$

The results obtained show that the compounds of the present invention are able to reduce the infection degree. Particularly, the compound of Example 1 showed to be the utmost effective, in fact it provided an infection reduction of over 70% already with the minimum dose used in the test.

Evaluation of the in vivo protection against septic shock

BALB/C mice (6 mice/group) weighting between 20 and 25 g, were intraperitoneally inoculated with 50 mg/kg of LPS (lipopolysaccharide-Sigma). The groups, except for the control, were inoculated with increasing doses of one of the compounds of the invention dissolved in physiologic solution having a final volume of 0.5 ml, at time 0 (i.e. together with LPS) or 30 minutes after the LPS inoculation. The mice were checked for 8 days to determined the survival percentage. Compound of Example 1 yields a survival percentage of about 65% at doses of 6.2 ug/mouse and 0.62 ug/mouse, and its isomer B yields a survival percentage of about 80% at a dose of 6.25 ug/mouse and of 75% at a dose of 62.5 ug/mouse.

In view of what said, the compounds of the present invention are useful in all the pathologic and non pathologic situations where it takes to strenght or restore the immune response both in therapy and in prophylaxis. Therefore, as examples of use of the present compounds there may be cited bacteric infections, mainly in case of septic shock, viral infections (herpes), parasitosis, infections due to acquired immuno-efficiency syndrome, prophylaxis in youth and elder, heavily burn, dialysis, tumours and transplantation. Moreover the compounds of the invention may be enployed as adjuvant in vaccines.

Also object of the present invention is the use of the new compounds as immuno-stimulating agents, as well as to all the industrial aspects connected to said use, including the pharmaceutical compositions containing the compounds of the invention. For the intended therapeutic uses, the compounds of formula I may be administered suitably formulated in pharmaceutical compositions according to what described, for example, in "Remington's Pharmaceutical Sciences Handbook", Mack Pub. Co., XVII ed., N.Y. USA. Obviously the posology will depend on several aspects such as the kind and severity of the case to be treated and the conditions of the patient (weight, age, sex, ecc.).

We claim:

1. Retroinverted tetrapeptides of the general formula

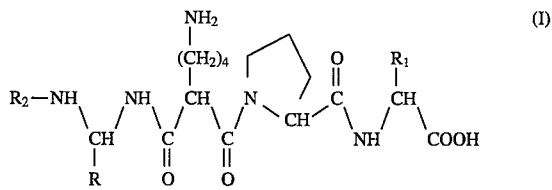

wherein R is a hydrogen atom or the side-chain of threonine; $R_1$ is the side-chain of arginine, leucine or glutamine; and $R_2$ is a hydrogen atom or a metabolically perishable acyl group; with the proviso that when $R_1$ is the side-chain of arginine, R cannot be the side-chain of threonine; diastereoisomeric forms and pharmacologically acceptable salt, esters and amides thereof.

2. Tetrapeptide according to claim 1 which is gGly-(R, S)mLys-Pro-Arg and the single diastereoisomeric forms.

3. Tetrapeptide according to claim 1 which is gThr-(R, S)mLys-Pro-Leu and the single diastereoisomeric forms.

4. Tetrapeptide according to claim 1 which is gThr-(R, S)mLys-Pro-Gln and the single diastereoisomeric forms.

5. A method for immunostimulation comprising administering to a subject in need thereof an effective amount of a compound of formula (I)

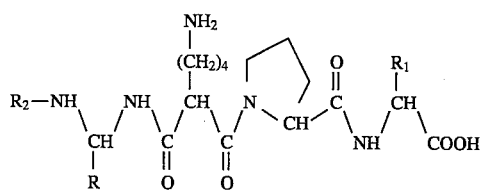 (I)

wherein R is a hydrogen atom or the side-chain of threonine; $R_1$ is the side-chain of arginine, leucine or glutamine; and $R_2$ is a hydrogen atom or a metabolically perishable acyl group; with the proviso that when $R_1$ is the side-chain of arginine, R cannot be the side-chain of threonine; diastereo-isomeric forms and pharmacologically acceptable salts, esters and amides thereof.

6. A pharmaceutical composition comprising an immunostimulating effective amount of at least one compound of claim 1.

7. The pharmaceutical composition of claim 6 further comprising a pharmaceutically acceptable eccipient.

* * * * *